(12) United States Patent
Trieselmann et al.

(10) Patent No.: US 7,214,698 B2
(45) Date of Patent: May 8, 2007

(54) BETA-AGONISTS, PROCESSES FOR PREPARING THEM AND THEIR USE AS PHARMACEUTICAL COMPOSITIONS

(75) Inventors: Thomas Trieselmann, Warthausen (DE); Bradford S. Hamilton, Biberach (DE); Dirk Stenkamp, Biberach (DE); Stephan Georg Mueller, Warthausen (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

(21) Appl. No.: 11/276,649

(22) Filed: Mar. 9, 2006

(65) Prior Publication Data

US 2006/0173061 A1    Aug. 3, 2006

Related U.S. Application Data

(62) Division of application No. 10/695,077, filed on Oct. 28, 2003, now abandoned.

(60) Provisional application No. 60/496,748, filed on Aug. 21, 2003.

(30) Foreign Application Priority Data

Oct. 31, 2002    (DE) ................................ 102 51 170

(51) Int. Cl.
*A61K 31/4164*    (2006.01)
(52) U.S. Cl. ...................... 514/399; 514/311
(58) Field of Classification Search ................ 514/311, 514/399
See application file for complete search history.

(56) References Cited

U.S. PATENT DOCUMENTS

| | | |
|---|---|---|
| 2,943,090 A | 6/1960 | Semb et al. |
| 3,092,636 A | 6/1963 | Heinzelman et al. |
| 4,647,563 A | 3/1987 | Schromm et al. |

FOREIGN PATENT DOCUMENTS

| | | |
|---|---|---|
| DE | 2115926 | 10/1972 |
| EP | 0008653 | 3/1980 |
| EP | 0177245 | 4/1986 |
| GB | 1200886 | 8/1970 |
| GB | 2356197 | 5/2001 |
| WO | 9529159 | 11/1995 |
| WO | 9721665 | 6/1997 |

OTHER PUBLICATIONS

Kawashima Kazu; Publication No. 08165276, Publication Date Jun. 25, 1996; 2-akylamino-1-phenylethanol derivative; Patent Abstract of Japan, vol. 1996, No. 10.

Robert Bruce Moffett; New Compounds with Possible Pharmacological Activity; Journal of Chemical and Engineering Data (1980), vol. 25, pp. 176-183; American Chemical Society.

James E. Clifton, et al; Arylethanolamines Derived from Salicylamide with alpha and beta-Adrenoceptor Blocking Activities. Preparation of Labetalol, Its Enantiomers, and Related Salicylamides; Journal of Medical Chemistry (1982), vol. 25, pp. 670-679; American Chemical Society.

*Primary Examiner*—Laura L. Stockton
(74) *Attorney, Agent, or Firm*—Michael P. Morris; Mary-Ellen M. Devlin; Alan R. Stempel

(57) ABSTRACT

The present invention relates to new beta-agonists of general formula 1:

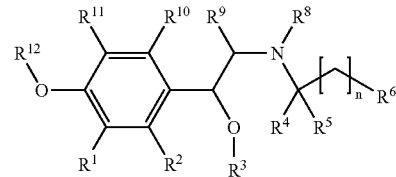

wherein the groups $R^1$ to $R^{12}$ have the meanings given in the claims and specification, the isomers thereof, processes for preparing these compounds and their use as pharmaceutical compositions.

6 Claims, No Drawings

BETA-AGONISTS, PROCESSES FOR PREPARING THEM AND THEIR USE AS PHARMACEUTICAL COMPOSITIONS

RELATED APPLICATIONS

This application is a division of application Ser. No. 10/695,077 filed Oct. 28, 2003, now abandoned which claimed benefit of provisional application Ser. No. 60/496,748 filed Aug. 21, 2003.

FIELD OF THE INVENTION

The present invention relates to new beta-agonists of general formula 1:

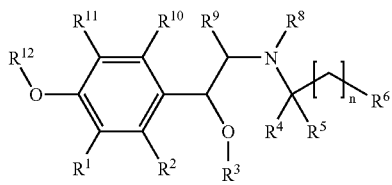

wherein the groups $R^1$ to $R^{12}$ have the meanings given in the claims and specification, the isomers thereof, processes for preparing these compounds and their use as pharmaceutical compositions.

BACKGROUND TO THE INVENTION

The treatment of type II diabetes and obesity is based primarily on reducing calorie intake and increasing physical activity. These methods are rarely successful in the longer term.

It is known that beta-3 receptor agonists have a significant effect on lipolysis, thermogenesis and the serum glucose level in animal models of type II diabetes (Arch JR. beta (3)-Adrenoceptor agonists: potential, pitfalls and progress, Eur J Pharmacol. Apr. 12, 2002; 440(2–3):99–107).

Compounds which are structurally similar to the compounds according to the invention and their broncholytic, spasmolytic and antiallergic activities were disclosed in DE 2833140, for example.

The aim of the present invention is to provide selective beta-3 agonists which can be used to prepare pharmaceutical compositions for the treatment of obesity and type II diabetes.

DETAILED DESCRIPTION OF THE INVENTION

Surprisingly it has been found that compounds of general formula (I) wherein the groups $R^1$ to $R^{12}$ are defined as hereinafter are effective as selective beta-3 agonists. Thus, the compounds according to the invention may be used to treat diseases connected with the stimulation of beta-3-receptors.

The present invention therefore relates to compounds of general formula (I)

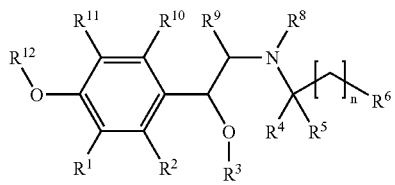

wherein
$R^1$, $R^2$, $R^{10}$, $R^{11}$ independently of one another denote a group selected from among hydrogen, halogen, CN, $NO_2$, and $-NHCXNH_2$ or a group selected from among optionally substituted $-COR^7$, $-COOR^7$, $-CONR^7R^{13}$, $-OR^{14}$, $NR^{13}R^{15}$, $C_1-C_{10}$-alkyl, $C_3-C_8$-cycloalkyl, $-NR^{16}CX-R^{17}$, $-NR^{18}CX-OR^{19}$, $-NR^{20}SO_mR^{21}$, $-SO_pNR^{22}R^{23}$ and $-SO_qR^{24}$,
m, p, q independently of one another denote 0, 1 or 2,
n denotes 0, 1, 2 or 3,
$R^3$ denotes hydrogen or a group selected from among optionally substituted $C_1-C_{10}$-alkyl, $C_6-C_{10}$-aryl, heterocyclyl, $C_3-C_8$-cycloalkyl, $-CX-C_1-C_{10}$-alkyl and $-CX-C_6-C_{14}$-aryl,
$R^4$, $R^5$ independently of one another denote hydrogen, halogen or optionally substituted $C_1-C_{10}$-alkyl,
or
$R^4$ and $R^5$ together denote a $C_3-C_8$-alkyl bridge,
$R^6$ denotes a group selected from among the general formulae

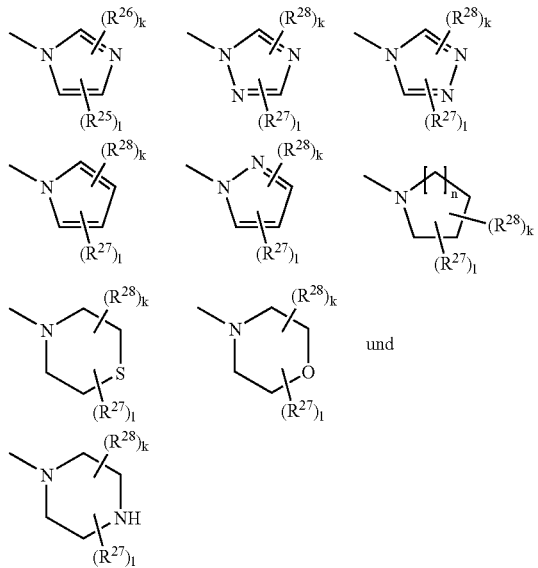

l,k independently of one another denote 1, 2 or 3,
$R^{25}$, $R^{26}$, $R^{27}$, $R^{28}$ independently of one another denote a group selected from among hydrogen, OH, halogen, CN and $NO_2$,
or
a group selected from among optionally substituted $C_1-C_{10}$-alkyl, $C_6-C_{18}$-aryl, heteroaryl, heterocyclyl, $-CX-R^{17}$, $-OR^{14}$, $NR^{13}R^{15}$, $C_2-C_8$-cycloalkyl, $-NR^{20}SO_mR^{21}$, $-SO_pNR^{22}R^{23}$, $-SO_qR^{24}$, $-NR^{18}CX-R^{19}$, $-NR^{18}CXOR^{17}$, while $R^{25}$ and $R^{26}$ cannot simultaneously denote hydrogen, R⁸ denotes hydrogen or a group selected from among optionally substituted $C_1$–$C_{10}$-alkyl, $C_6$–$C_{18}$-aryl, —$SO_q$—$C_1$–$C_{10}$-alkyl, —$SO_q$—$C_6$–$C_{14}$-aryl, —CX—$C_1$–$C_{10}$-alkyl, —CX—$C_6$–$C_{14}$-aryl, $C_6$–$C_{10}$-aryl, heterocyclyl and $C_3$–$C_8$-cycloalkyl R⁹ denotes hydrogen or a group selected from among optionally substituted $C_1$–$C_{10}$-alkyl, $C_6$–$C_{14}$-aryl, heteroaryl, $C_3$–$C_8$-cycloalkyl and heterocycloalkyl, R¹² denotes hydrogen or a group selected from among optionally substituted benzyl, $C_1$–$C_{12}$-alkyl and $C_6$–$C_{14}$-aryl, R⁷, R¹³, R¹⁵, R¹⁶, R¹⁸, R²⁰ R²², R²³ independently of one another denote hydrogen, or
a group selected from among optionally substituted $C_1$–$C_{10}$-alkyl, $C_6$–$C_{14}$-aryl, heterocyclyl and $C_3$–$C_8$-cycloalkyl R¹⁴, R¹⁹, R²⁹ independently of one another denote hydrogen or a group selected from among optionally substituted $C_1$–$C_{10}$-alkyl, $C_6$–$C_{14}$-aryl, $C_3$–$C_8$-cycloalkyl, heteroaryl, heterocyclyl, —$CXNR_{13}R_{15}$, —$CXR_7$ R¹⁷ denotes a group selected from among $C_1$–$C_{10}$-alkyl, $C_6$–$C_{14}$-aryl, heterocyclyl, heteroaryl and $C_3$–$C_8$-cycloalkyl R²¹, R²⁴ independently denote hydrogen or OH, or a group selected from among optionally substituted $N(C_1$–$C_{10}$-alkyl$)_2$, $N(C_3$–$C_8$-cycloalkyl), $C_1$–$C_{10}$-alkyl, $C_6$–$C_{14}$-aryl, heterocyclyl, heteroaryl and $C_3$–$C_8$-cycloalkyl
and X denotes O, S or NR²⁹, optionally in the form of the tautomers, the racemates, the enantiomers, the diastereomers and the mixtures thereof, as well as optionally the pharmacologically acceptable acid addition salts thereof.

Preferred are compounds wherein

R¹⁰, R¹¹ independently of one another denote hydrogen or halogen, m, p, q denote 0, 1 or 2 n denotes 0, 1, 2 or 3

R³ denotes hydrogen or $C_1$–$C_5$-alkyl

R⁴, R⁵ independently of one another denote hydrogen or $C_1$–$C_5$-alkyl,

R⁸ denotes a group selected from among hydrogen, $C_1$–$C_5$-alkyl, —$SO_q$—$C_1$–$C_5$-alkyl, —$SO_q$—$C_6$–$C_{14}$-aryl, phenyl and $C_3$–$C_6$-cycloalkyl R⁹ denotes hydrogen or $C_1$–$C_{10}$-alkyl R¹² denotes hydrogen or benzyl R¹³, R¹⁵, R¹⁶, R¹⁸ independently of one another denote a group selected from among hydrogen, $C_1$–$C_5$-alkyl, $C_3$–$C_6$-cycloalkyl and phenyl R¹⁴, R¹⁹ independently of one another denote hydrogen or $C_1$–$C_5$-alkyl,
and R¹⁷ denotes optionally substituted $C_1$–$C_5$-alkyl or $C_6$–$C_{10}$-aryl.

Also preferred are compounds wherein

R¹⁰, R¹¹ denotes hydrogen m, p, q denote 0, 1 or 2 n denotes 0, 1, 2 or 3

R³ denotes hydrogen

R⁴, R⁵ independently of one another denote hydrogen or methyl,

R⁸ denotes hydrogen, —$SO_q$—$C_6$–$C_{14}$-aryl or —$SO_2$—$C_1$–$C_5$-alkyl

R⁹ denotes hydrogen

R¹² denotes hydrogen or benzyl,

R¹³, R¹⁵, R¹⁶, R¹⁸ independently of one another denote a group selected from among hydrogen, $C_1$–$C_{15}$-alkyl and phenyl, R¹⁴, R¹⁹ independently of one another denote hydrogen or $C_1$–$C_5$-alkyl,
and R¹⁷ denotes $C_1$–$C_5$-alkyl or $C_6$–$C_{14}$-aryl.

Particularly preferred are compounds wherein

R¹ denotes a group selected from among hydrogen, $NO_2$, $NH_2$, —NHCX—R¹⁷ and —$NHSO_2R^{21}$.

R² denotes hydrogen or halogen n denotes 2,

R³ denotes hydrogen

R⁴, R⁵ denote hydrogen or methyl

R⁶ denotes a group selected from among the general formulae l,k denotes 1

R²⁶, R²⁷ denotes hydrogen,

R⁸ denotes hydrogen or —$SO_2CH_3$,

R⁹ denotes hydrogen,

R¹⁰, R¹¹ denote hydrogen, and

R¹² denotes hydrogen or benzyl.

Also particularly preferred are compounds wherein

R⁶ denotes a group selected from among the general formulae

Particularly preferred are compounds wherein
$R^6$ denotes an optionally substituted group of formula (j)

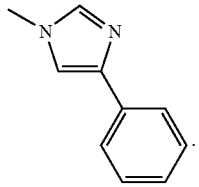

(j)

The invention further relates to compounds of formula (I) for use as pharmaceutical compositions.

The invention further relates to compounds of formula (I) for use as pharmaceutical compositions with a selective beta-3-agonistic activity.

The invention further relates to the use of a compound of formula (I) for preparing a pharmaceutical composition for the treatment and/or prevention of diseases connected with the stimulation of beta-3-receptors.

The invention further relates to a method for the treatment and/or prevention of diseases connected with the stimulation of beta-3-receptors, in which a patient is given an effective amount of a compound of formula I.

Of particular importance according to the invention is a pharmaceutical composition containing as active substance one or more compounds of general formula (I) or the physiologically acceptable salts thereof, optionally combined with conventional excipients and/or carriers.

Also of particular importance is a pharmaceutical composition containing as active substance one or more compounds of general formula (I) according to one of claims 1 to 6 or the physiologically acceptable salts thereof and one or more active substances selected from among antidiabetics, inhibitors of protein tyrosinephosphatase 1, substances which influence deregulated glucose production in the liver, lipid lowering agents, cholesterol absorption inhibitors, HDL-raising compounds, active substances for the treatment of obesity and modulators or stimulators of the adrenergic receptor via alpha 1 and alpha 2 as well as beta 1, beta 2 and beta 3 receptors.

The invention further relates to a process for preparing a compound of general formula (I),

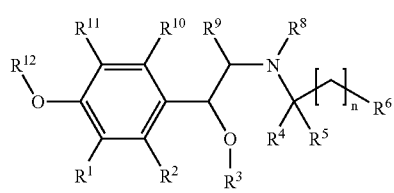

wherein
$R^1$—$R^{28}$ and X may be as hereinbefore defined, wherein a compound of general formula (II)

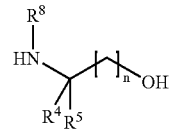

(II)

where
$R^4$ and $R^5$ may be as hereinbefore defined, is converted by means of a chlorinating agent into a compound of formula (III)

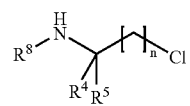

(III)

the compound of formula (III), optionally provided with an amino protective group, is reacted with an optionally substituted compound selected from among the general formulae (IVa) to (IVi)

(IV)

a)

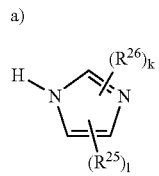

b)

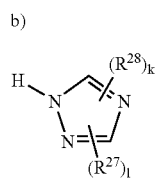

c)

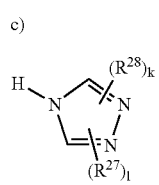

d)

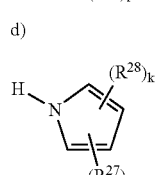

e)

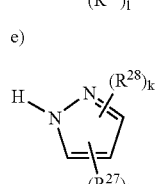

-continued f)

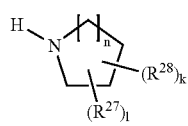

g)

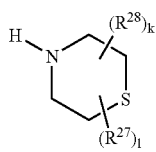

h)

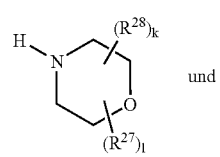

und i)

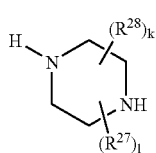

wherein k, l, R²⁷ and R²⁸ are as hereinbefore defined, and the product of formula (V)

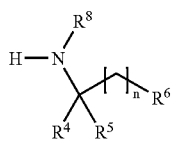 (V)

wherein n, R⁴, R⁵, R⁶ and R⁸ are as hereinbefore defined, is reacted with a compound of formula (VIa) to (VIc)

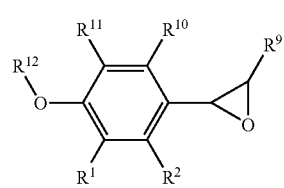 (VIa)

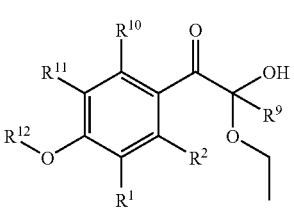 (VIb)

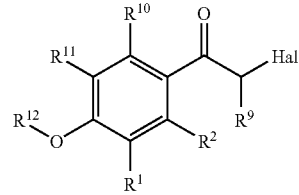 (VIc)

wherein $R^1$, $R^2$, $R^9$ and $R^{10}$ to $R^{12}$ are as hereinbefore defined.

The term alkyl groups, including alkyl groups which are a part of other groups, denotes branched and unbranched alkyl groups with 1 to 10 carbon atoms, preferably 1–6, most preferably 14 carbon atoms, such as, for example: methyl, ethyl, propyl, butyl, pentyl, hexyl, heptyl, octyl, nonyl and decyl. Unless otherwise stated, the above-mentioned terms propyl, butyl, pentyl, hexyl, heptyl, octyl, nonyl and decyl include all the possible isomeric forms. For example, the term propyl includes the two isomeric groups n-propyl and iso-propyl, the term butyl includes n-butyl, iso-butyl, sec. butyl and tert-butyl, the term pentyl includes iso-pentyl, neopentyl, etc.

In the above-mentioned alkyl groups one or more hydrogen atoms may optionally be replaced by other groups. For example these alkyl groups may be substituted by the halogen atoms fluorine, chlorine, bromine or iodine. Preferably the substituents are fluorine or chlorine, most preferably chlorine. All the hydrogen atoms of the alkyl group may optionally also be replaced.

Similarly, in the above-mentioned alkyl groups, unless otherwise stated, one or more hydrogen atoms may optionally be replaced, for example, by an optionally substituted group selected from among OH, $NO_2$, CN, $-O-C_1-C_5$-alkyl, preferably —O-methyl or —O-ethyl, $O-C_6-C_{14}$-aryl, preferably O-phenyl, O-heteroaryl, preferably O-thienyl, O-thiazolyl, O-imidazolyl, O-pyridyl, O-pyrimidyl or O-pyrazinyl, saturated or unsaturated O-heterocycloalkyl, preferably O-pyrazolyl, O-pyrrolidinyl, O-piperidinyl, O-piperazinyl or O-tetrahydro-oxazinyl, $C_6-C_{14}$-aryl, preferably phenyl, heteroaryl, preferably thienyl, thiazolyl, imidazolyl, pyridyl, pyrimidyl or pyrazinyl, saturated or unsaturated heterocycloalkyl, preferably pyrazolyl, pyrrolidinyl, piperidinyl, piperazinyl or tetrahydro-oxazinyl, an amine group, preferably methylamine, benzylamine, phenylamine or heteroarylamine, saturated or unsaturated bicyclic ring systems, preferably benzimidazolyl and $C_3-C_8$-cycloalkyl, preferably cyclohexyl or cyclopropyl.

The term aryl denotes an aromatic ring system with 6 to 18 carbon atoms, preferably 6 to 14 carbon atoms, preferably 6 or 10 carbon atoms, most preferably phenyl, which, unless otherwise stated, may carry one or more of the following substituents, for example: OH, $NO_2$, CN, $-OCHF_2$, $-OCF_3$, $-NH_2$, halogen, for example fluorine, chlorine, bromine or iodine, preferably fluorine or chlorine, particularly preferably fluorine, $C_1-C_{10}$-alkyl, preferably $C_1-C_5$-alkyl, preferably $C_1-C_3$-alkyl, most preferably methyl or ethyl, $-O-C_1-C_3$-alkyl, preferably —O-methyl or —O-ethyl, —COOH or $-CONH_2$.

Examples of heteroaryl groups are 5–10-membered mono- or bicyclic heteroaryl rings wherein up to three C atoms may be replaced by one or more heteroatoms selected from among oxygen, nitrogen or sulphur, for example furan, thiophene, pyrrole, pyrazole, imidazole, triazole, tetrazole, pyridine, pyridazine, pyrimidine, pyrazine, triazine, oxazole, isoxazole, thiazole, thiadiazole, oxadiazole, while each of the above-mentioned heterocycles may optionally also be annellated to a benzene ring, preferably benzimidazole, and unless otherwise specified these heterocycles may for example carry one or more of the following substituents: OH, $NO_2$, CN, —$NH_2$, halogen, preferably fluorine or chlorine, $C_1$–$C_{10}$-alkyl, preferably $C_1$–$C_5$-alkyl, preferably $C_1$–$C_3$-alkyl, particularly preferably methyl or ethyl, —O—$C_1$–$C_3$-alkyl, preferably —O-methyl or —O-ethyl, —COOH, —$COOCH_3$, —$CONH_2$, —SO-alkyl, —$SO_2$-alkyl, —$SO_2H$, —$SO_3$-alkyl or optionally substituted phenyl.

Examples of cycloalkyl groups are saturated or unsaturated cycloalkyl groups with 3 to 8 carbon atoms for example cyclopropyl, cyclobutyl, cyclopentyl, cyclopentenyl, cyclohexyl, cyclohexenyl, cycloheptyl or cyclooctyl, preferably cyclopropyl, cyclopentyl or cyclohexyl, while each of the above-mentioned cycloalkyl groups may optionally also carry one or more substituents or be annellated to a benzene ring.

Unless otherwise stated in the definitions, examples of heterocycloalkyl groups include 5-, 6- or 7-membered, saturated or unsaturated heterocycles which may contain nitrogen, oxygen or sulphur as heteroatoms, for example tetrahydrofuran, tetrahydrofuranone, γ-butyrolactone, α-pyran, γ-pyran, dioxolane, tetrahydropyran, dioxane, dihydrothiophene, thiolane, dithiolane, pyrroline, pyrrolidine, pyrazoline, pyrazolidine, imidazoline, imidazolidine, tetrazole, piperidine, pyridazine, pyrimidine, pyrazine, piperazine, triazine, tetrazine, morpholine, thiomorpholine, diazepan, oxazine, tetrahydro-oxazinyl, isothiazole and pyrazolidine, preferably pyrazolyl, pyrrolidinyl, piperidinyl, piperazinyl or tetrahydro-oxazinyl, while the heterocyclic group may optionally be substituted.

The halogen is generally fluorine, chlorine, bromine or iodine, preferably chlorine or fluorine, particularly preferably fluorine.

The compounds according to the invention may be present in the form of the individual optical isomers, mixtures of the individual enantiomers, diastereomers or racemates, in the form of the tautomers and also in the form of the free bases or the corresponding acid addition salts with pharmacologically acceptable acids—such as for example acid addition salts with hydrohalic acids, for example hydrochloric or hydrobromic acid, or organic acids, such as for example oxalic, fumaric, diglycolic, formic, malic, benzoic, benzenesulphonic, camphorsulphonic, acetic, ethanesulphonic, glutamic, maleic, mandelic, lactic, phosphoric, nitric, sulphuric, succinic, para-toluenesulphonic, trifluoroacetic, tartaric, citric or methanesulphonic acid.

The substituent $R^1$ may denote a group selected from among hydrogen, halogen, preferably fluorine or chlorine, CN, $NO_2$, and —$NHCXNH_2$, preferably $NHCONH_2$ or a group selected from among optionally substituted —$COR^7$, —$COOR^7$, —$CONR^7R^{13}$, —$OR^{14}$, preferably OH, $NR^{13}R^{15}$, $C_1$–$C_{10}$-alkyl, $C_3$–$C_8$-cycloalkyl, —$NR^{16}CX$—$R^{17}$, —$NR^{18}CX$—$OR^{19}$, —$NR^{20}SO_mR^{21}$, —$SO_pNR^{22}R^{23}$, preferably —$SO_2NHR^{23}$, and —$SO_qR^2$.

In particular the substituent $R^1$ denotes —$NR^{20}SO_mR^{21}$, preferably —$NHSO_mR^{21}$.

The substituent $R^2$ may denote a group selected from among hydrogen, halogen, preferably fluorine or chlorine, CN, $NO_2$, and —$NHCXNH_2$, preferably $NHCONH_2$ or a group selected from among optionally substituted —$COR^7$, —$COOR^7$, —$CONR^7R^{13}$, —$OR^{14}$, preferably OH, $NR^{13}R^{15}$, $C_1$–$C_{10}$-alkyl, $C_3$–$C_8$-cycloalkyl, —$NR^{16}CX$—$R^{17}$, —$NR^{18}CX$—$OR^{19}$, $NR^{20}SO_mR^{21}$, —$SO_pNR^{22}R^{23}$, preferably —$SO_2NHR^{23}$ and —$SO_qR^{23}$.

In particular the substituent $R^2$ denotes hydrogen or fluorine.

The substituents $R^{10}$ and $R^{11}$ may be identical or different and denote a group selected from among hydrogen, halogen, preferably fluorine or chlorine, CN, $NO_2$, and —NHCXNH$_2$, preferably NHCONH$_2$ or a group selected from among optionally substituted —$COR^7$, —$COOR^7$, —$CONR^7R^{13}$, —$OR^{14}$, preferably OH, $NR^{13}R^{15}$, $C_1$–$C_{10}$-alkyl, $C_3$–$C_8$-cycloalkyl, —$NR^{16}CX$—$R^{17}$, —$NR^{18}CX$—$OR^{19}$, —$NR^{20}SO_mR^{21}$, —$SO_pNR^{22}R^{22}R^{23}$ preferably —$SO_2NHR^{23}$ and —$SO_qR^2$. Particularly preferably, the substituents $R^{10}$ and $R^{11}$ denote hydrogen.

The variables m, p and q may represent 0, 1 or 2, preferably 2.

The variable n may represent 0, 1, 2 or 3, preferably 2.

The substituent $R^3$ may denote hydrogen or a group selected from among optionally substituted $C_1$–$C_{10}$-alkyl, $C_6$–$C_{10}$-aryl, heterocyclyl and $C_3$–$C_8$-cycloalkyl, —CX—$C_1$–$C_{10}$-alkyl, —CX—$C_6$–$C_{14}$-aryl.

Preferably the substituent $R^3$ denotes hydrogen.

The substituents $R^4$ and $R^5$ may be identical or different and denote hydrogen, halogen or optionally substituted $C_1$–$C_{10}$-alkyl, preferably hydrogen or $C_1$–$C_{10}$-alkyl, particularly preferably hydrogen or methyl, or $R^4$ and $R^5$ together may form a $C_3$–$C_8$-alkyl bridge, preferably a cyclohexyl, cyclopentyl or cyclopropyl bridge.

The substituent $R^6$ may denote a group selected from among the general formulae

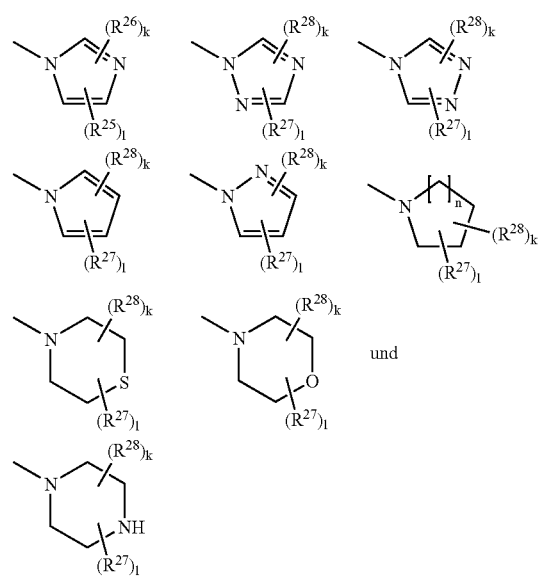

while the variables l and k independently of one another denote 1,2 or 3, preferably 1.

Particularly preferably, $R^6$ denotes

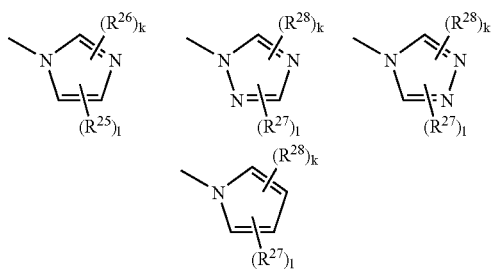

More preferably, $R^6$ denotes

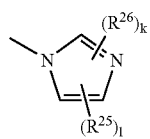

The substituents $R^{25}$, $R^{26}$, $R^{27}$, $R^{28}$ may be identical or different and denote a group selected from among hydrogen, OH, halogen, CN and $NO_2$,
or
a group selected from among optionally substituted $C_1$–$C_{10}$-alkyl, $C_6$–$C_{18}$-aryl, preferably phenyl, heteroaryl, preferably pyridyl, heterocyclyl, —CX—$R^{17}$, —$OR^{14}$, $NR^{13}R^{15}$, $C_2$–$C_8$-cycloalkyl, —$NR^{20}SO_mR^{21}$, —$SO_pNR^{22}R^{23}$, —$SO_qR^{24}$, —$NR^{18}CX$—$R^{19}$, —$NR^{18}CXOR^{17}$, while $R^{25}$ and $R^{26}$ cannot simultaneously denote hydrogen.

The substituent $R^8$ may represent hydrogen or a group selected from among optionally substituted $C_1$–$C_{10}$-alkyl, $C_6$–$C_{18}$-aryl, —$SO_q$-$C_1$–$C_{10}$-alkyl, —$SO_q$—$C_6$–$C_{14}$-aryl, —CX—$C_1$–$C_{10}$-alkyl, —CX—$C_6$–$C_{14}$-aryl, $C_6$–$C_{10}$-aryl, heterocyclyl and $C_3$–$C_8$-cycloalkyl, preferably hydrogen or —$SO_2CH_3$.

The substituent $R^9$ may represent hydrogen or a group selected from among optionally substituted $C_1$–$C_{10}$-alkyl, $C_6$–$C_{14}$-aryl, heteroaryl, $C_3$–$C_8$-cycloalkyland heterocycloalkyl, preferably hydrogen.

The substituent $R^{12}$ may represent hydrogen or a group selected from among optionally substituted benzyl, $C_1$–$C_{12}$-alkyl and $C_6$–$C_{14}$-aryl, CX—$C_1$–$C_{12}$-alkyl and CX—$C_6$–$C_{14}$-aryl, preferably hydrogen.

The substituents $R^7$, $R^{13}$, $R^{15}$, $R^{16}$, $R^{18}$, $R^{20}$, $R^{22}$, $R^{23}$ and $R^{24}$ may be identical or different and represent hydrogen, or a group selected from among optionally substituted $C_1$–$C_{10}$-alkyl, $C_6$–$C_{14}$-aryl, heterocyclyl and $C_3$–$C_8$-cycloalkyl.

Particularly preferably, the substituent $R^{20}$ denotes methyl, ethyl or isopropyl.

The substituents $R^{14}$, $R^{19}$ and $R^{29}$ may be identical or different and denote hydrogen or a group selected from among optionally substituted $C_1$–$C_{10}$-alkyl, preferably methyl or difluoromethyl, $C_6$–$C_{14}$-aryl, $C_3$–$C_8$-cycloalkyl, heteroaryl, heterocyclyl, —$CXNR_{13}R_{15}$, particularly preferably the substituent $R^{14}$ denotes methyl or difluoromethyl.

The substituent $R^{17}$ may denote a group selected from among $C_1$–$C_{10}$-alkyl, preferably methyl or ethyl, $C_6$–$C_{14}$-aryl, heterocyclyl, heteroaryl and $C_3$–$C_8$-cycloalkyl.

The substituent $R^{21}$ may represent hydrogen or OH, or a group selected from among optionally substituted $N(C_1$–$C_{10}$-alkyl$)_2$, $N(C_3$–$C_8$-cycloalkyl), $C_1$–$C_{10}$-alkyl, $C_6$–$C_{14}$-aryl, heterocyclyl, heteroaryl and $C_3$–$C_8$-cycloalkyl.

X may represent O, S or $NR^{29}$, preferably O.

The compounds according to the invention may be prepared by the methods of synthesis described hereinafter, where formulae (I) to (IV) and the substituents of general formulae $R^1$ to $R^{12}$ have the above-mentioned meanings. These processes are intended as an illustration of the invention without restricting it to their content.

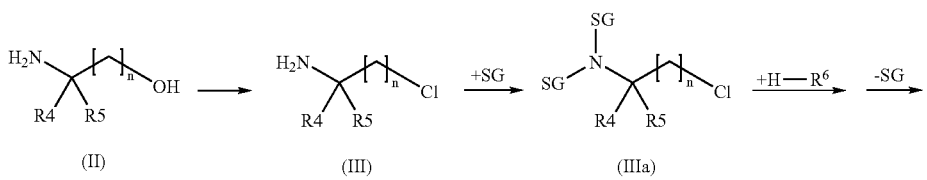

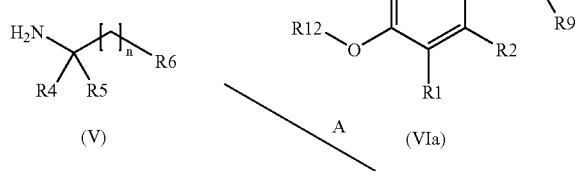

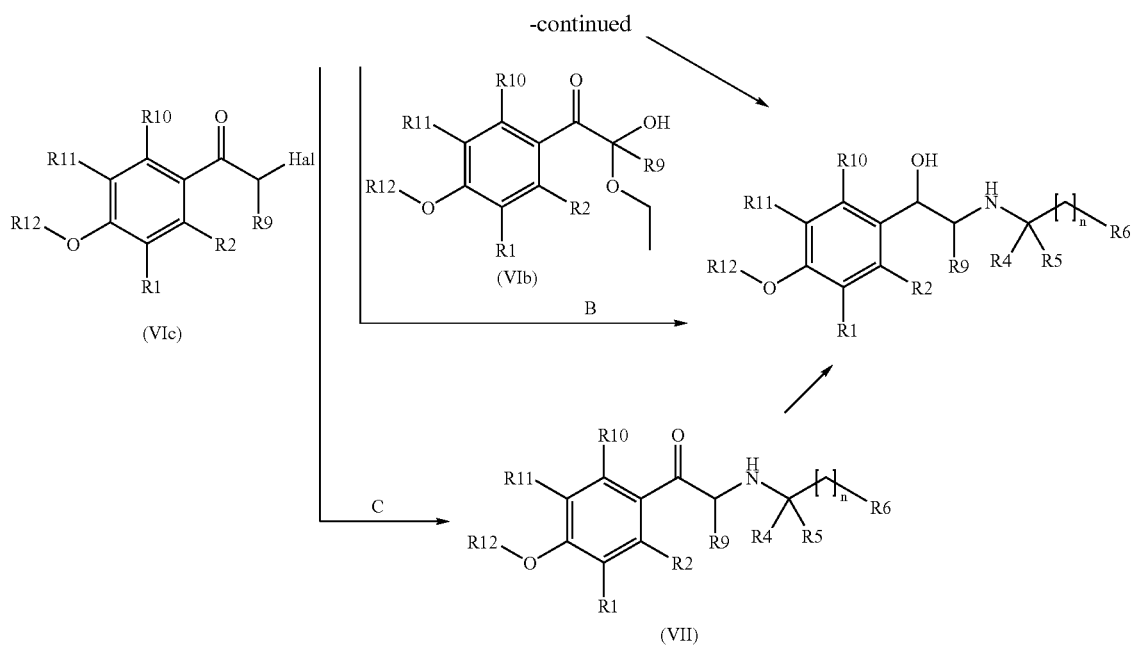

SG = Schutzgruppe
SG = protective group

Synthesis of 3-chloro-propylamine-hydrochloride (Compound III)

A compound of formula (II) is converted into a compound of formula (III) using a chlorinating agent.

Compound (II) may be prepared by methods known from the literature, for example DE 2200108 (Pander, Hans J. 3-amino-3-methyl-1-butanol, Ger. Offen. (1973), 6 pp.).

About 0.5 mol of compound (II) are dissolved or suspended in about 100 to 300 ml of a solvent, preferably in methylene chloride/dimethylformamide (50:1), pyridine, carbon tetrachloride, chloroform or dichloromethane. At about −3 to 5° C., preferably at 0° C., 0.4 to 0.9 mol, preferably 0.6 mol of a chlorinating agent, preferably thionyl chloride, N-chlorosuccinimide, para-toluenesulphonic acid chloride, methanesulphonic acid chloride/lithium chloride or zinc(II)chloride/triphenylphosphine/diethyldiazodicarboxylate, most preferably thionyl chloride, are added dropwise to the mixture, with stirring. The solvent is removed, the residue is washed with acetonitrile for example and dried.

Synthesis of the Dichlorobenzylidenamine of Compound (III)

The base is liberated from about 80–90, preferably 84.0 mmol of 3-chloro-1,1-dimethylpropylamine-hydrochloride by known methods. The free base is dissolved in about 50 mL of a solvent, preferably toluene, diethylethylether, tetrahydrofuran, dimethylsulphoxide, dimethylformamide or methylene chloride and about 60 to 100 mmol, preferably 80.0 mmol of 2,6-dichlorobenzaldehyde are added at ambient temperature, with stirring. The reaction mixture is stirred for 5 to 20 h, preferably for 15 h at ambient temperature, dried again and the solvent is removed. The corresponding dichlorobenzylidenamine of compound (III) is obtained.

Synthesis of the Dichlorobenzylidenamine of Compound (V)

30 to 45 mmol, preferably 39.0 mmol of a base, for example sodium hydride, are added to a solution of 25 to 40 mmol, preferably 33.0 mmol, of one of the compounds (IVa) to (IVi) in about 25 to 100 ml, preferably 50 mL of a solvent, for example tetrahydrofuran, dimethylsulphoxide, dimethylformamide or N-methylpyrrolidine, preferably 1,3-dimethyl-3,4,5,6-tetrahydro-2(1H)-pyrimidone at 5 to 15° C., preferably about 10° C., with stirring. After the addition has ended the reaction mixture is stirred for 1 h at ambient temperature and then 35 to 45 mmol, preferably 39.0 mmol of the dichlorobenzylidenamine of compound (III), dissolved in a solvent, preferably about 50 mL of 1,3-dimethyl-3,4,5,6-tetrahydro-2(1H)-pyrimidone, as well as 2 to 4 mmol, preferably about 3.3 mmol of tetrabutylammonium iodide are added. The reaction mixture is stirred for about 5 to 20 hours, preferably 18 h at ambient temperature, then about 4 h at 80° and then poured into about 200 mL ice water/ethyl acetate (1:1). The phases are separated and the aqueous phase is extracted with ethyl acetate. The combined organic phases are dried and the solvent is eliminated. The residue is combined with hydrochloric acid and stirred for about 1 h at about 100° C. The reaction mixture is cooled to about 0° C., combined with ethyl acetate and the pH is adjusted to 10, for example, with sodium hydroxide solution. The phases are separated and the aqueous phase is extracted with ethyl acetate. The combined organic phases are dried and the solvent is eliminated using the rotary evaporator. The residue is purified by chromatography, for example. About 430 mmol of compound (V) are obtained.

Synthesis of Compound (I):

The base is liberated from about 3 mmol of compound (V) using known methods. The free base is dissolved in methylene chloride and at ambient temperature about 2.6 mmol of a compound of formula (VIa–c) and about 2.6 mmol of ytterbium(III)trifluoromethanesulphonate are added, with stirring. The reaction mixture is stirred for about 3 days at ambient temperature and then water is added. The phases are separated and the aqueous phase is extracted with methylene chloride, for example. The combined organic phases are dried and the solvent is eliminated. The residue is purified by chromatography, for example.

About 0.1 mmol platinum(IV)oxide are added to a solution of about 0.3 mmol of the purified residue in for example about 10 mL tetrahydrofuran/toluene (1:1). The reaction mixture is shaken in an autoclave under a hydrogen pressure of about 10 psi at ambient temperature for about 5 to 20 h, preferably 16 h. The platinum(IV)oxide is filtered off and the filtrate is freed from solvent. Compound I is thus obtained.

The new compounds of general formula (I) may be synthesised analogously to the following examples of synthesis. These Examples are intended only as examples of procedures to illustrate the invention in more detail without restricting it to their contents.

EXAMPLE 1 a) Synthesis of 3-chloro-1,1-dimethylpropylamine-hydrochloride 48.7 mL (668 mmol) of thionyl chloride were slowly added dropwise to a solution of 53.0 g (514 mmol) of 3-amino-3-methyl-butanol in 255 mL methylene chloride/dimethylformamide (50:1) at 0° C. with vigorous stirring. After the addition was complete the reaction mixture was refluxed for 1 h and then stirred for 16 h at ambient temperature. The solvent was removed and the residue was combined with 50 mL acetonitrile with stirring. The solid was filtered off and dried at 45° C. for 18 h. 67.9 g (430 mmol, 84%) of 3-chloro-1,1-dimethylpropylamine-hydrochloride were obtained as a colourless solid.

MS: (M+H)=122/124(Cl)

b) Synthesis of (3-chloro-1,1-dimethylpropyl)-(2,6-dichlorobenzylidene)-amine 13.3 g (84.0 mmol) of 3-chloro-1,1-dimethyl propylamine-hydrochloride were added to 84.0 mL sodium hydroxide solution (1 M) at 0° C. with vigorous stirring. The reaction mixture was stirred for 30 min at 0° C. and then combined with 50 mL methylene chloride. The phases were separated and the aqueous phase was twice extracted with 35 mL methylene chloride. The combined organic phases were dried over magnesium sulphate and at ambient temperature combined with 14.2 g (81.0 mmol) of 2,6-dichlorobenzaldehyde with stirring. The reaction mixture was stirred for 18 h at ambient temperature, dried again with magnesium sulphate and the solvent was removed. 22.3 g (80.0 mmol, 99%) (3-chloro-1,1-dimethylpropyl)-(2,6-dichlorobenzylidene)-amine were obtained as a yellowish oil.

MS: (M+H)=278/280/282 (Cl3)

c) Synthesis of 1,1-dimethyl-3-(4-phenyl-imidazol-1-yl)-propylamine 1.60 g (50% in oil, 39.0 mmol) sodium hydride were slowly added to a solution of 4.80 g (33.0 mmol) of 4-phenylimidazole in 50 mL of 1,3-dimethyl-3,4,5,6-tetrahydro-2(1H)-pyrimidone at 10° C. with vigorous stirring. After the addition was complete the reaction mixture was stirred for 1 h at ambient temperature, and then 10.9 g (39.0 mmol) of (3-chloro-1,1-dimethylpropyl)-(2,6-dichlorobenzylidene)-amine dissolved in 50 mL of 1,3-dimethyl-3,4,5,6-tetrahydro-2(1H)-pyrimidone and also 1.20 g (3.33 mmol) of tetrabutylammonium iodide were added. The reaction mixture was stirred for 18 h at ambient temperature, stirred for 4 h at 80° and then poured into 200 mL of ice water/ethyl acetate (1:1). The phases were separated and the aqueous phase was extracted three times with 50 mL of ethyl acetate. The combined organic phases were dried over magnesium sulphate and the solvent was removed. The residue was combined with 11 mL hydrochloric acid (3.5 M) and stirred for 1 h at 100° C. The reaction mixture was cooled to 0° C., combined with 50 ml of ethyl acetate and the pH was adjusted to 10 with sodium hydroxide solution (1M). The phases were separated and the aqueous phase was extracted three times with 50 mL ethyl acetate. The combined organic phases were dried over magnesium sulphate and the solvent was removed. The residue was purified by flash column chromatography [methylene chloride/methanol/ammonia (90:10:1)]. 67.9 g (430 mmol, 83%) 3-chloro-1,1-dimethylpropylamine-hydrochloride were obtained as a colourless solid.

MS: (M+H)=230

$R_f$: 0.30 [methylene chloride/methanol/ammonia (90:10:1)]

d) Synthesis of (R)-1-(4-benzyloxy-3-nitrophenyl)-2-[1,1-dimethyl-3-(4-phenylimidazol-1-yl)-propylamino]-ethanol 0.90 g (3.1 mmol) of 3-chloro-1,1-dimethylpropylamine-hydrochloride were added to 10 mL sodium hydroxide solution (1 M) at 0° C. with vigorous stirring. The reaction mixture was stirred for 30 min at 0° C. and then combined with 20 mL methylene chloride. The phases were separated and the aqueous phase was extracted twice with 20 mL of methylene chloride. The combined organic phases were dried over magnesium sulphate and the solvent was eliminated using a rotary evaporator. The residue was dissolved in 5.0 mL of methylene chloride and combined at ambient temperature with 0.70 g (2.6 mmol) (R)-2-(4-benzyloxy-3-nitrophenyl)-oxirane and 0.20 g (0.26 mmol) ytterbium (III) trifluoromethanesulphonate, with vigorous stirring. The reaction mixture was stirred for 3 d at ambient temperature and then combined with 30 mL water/methylene chloride (1:1). The phases were separated and the aqueous phase was extracted twice with 20 mL methylene chloride. The combined organic phases were dried over magnesium sulphate and the solvent was eliminated using a rotary evaporator. The residue was purified by flash column chromatography [methylene chloride/methanol/ammonia (90:10:1)]. 0.40 g (0.86 mmol, 33%) of (R)-1-(4-benzyloxy-3-nitrophenyl)-2-[1,1-dimethyl-3-(4-phenylimidazol-1-yl)-propylamino]-ethanol was obtained as a yellowish solid.

MS: (M+H)=501, (M−H)=499

$R_f$: 0.27 [methylene chloride/methanol/ammonia (90:10:1)]

e) Synthesis of (R)-1-(3-amino-4-benzyloxyphenyl)-2-[1,1-dimethyl-3-(4-phenylimidazol-1-yl)-propylamino]-ethanol 0.025 g (0.11 mmol) platinum(IV)oxide were added to a solution of 0.15 g (0.28 mmol) (R)-1-(4-benzyloxy-3-nitrophenyl)-2-[1,1-dimethyl-3-(4-phenylimidazol-1-yl)-propylamino]-ethanol in 10 mL tetrahydrofuran/toluene (1:1). The reaction mixture was shaken in an autoclave under a hydrogen pressure of 10 psi at ambient temperature for 16 h. The hydrogen pressure was released, the platinum(IV)oxide was filtered off and the filtrate was freed from solvent. 0.14 g (0.28 mmol, 99%) (R)-1-(3-amino-4-benzyloxyphenyl)-2-[1,1-dimethyl-3-(4-phenylimidazol-1-yl)-propylamino]-ethanol were obtained as a brown oil.

MS: (M+H)=471, (M−H)=469

$R_f$: 0.26 [ethyl acetate/methanol/ammonia (90:10:1)]

f) Synthesis of (R)—N-(2-benzyloxy-5-{2-[1,1-dimethyl-3-(4-phenylimidazol-1-yl)-propylamino]-1-hydroxyethyl}-phenyl)-benzenesulphonamide 0.10 mL (41 mmol) benzenesulphonic acid chloride were slowly added at 0° C. to a solution of 0.20 g (41 mmol) (R)-1-(3-amino-4-benzyloxyphenyl)-2-[1,1-dimethyl-3-(4-phenylimidazol-1-yl)-propylamino]-ethanol in 5 mL pyridine with vigorous stirring. After the addition was complete the reaction mixture was stirred for 4 h at 0° C. and then poured into 40 mL ice water/ethyl acetate (1:1). The phases were separated and the aqueous phase was extracted three times with 20 mL of ethyl acetate. The combined organic phases were dried over magnesium sulphate and the solvent was removed using the rotary evaporator. 0.14 g (0.28 mmol, 99%) (R)—N-(2-benzyloxy-5-{2-[1,1-dimethyl-3-(4-phenylimidazol-1-yl)-propylamino]-1-hydroxyethyl}-phenyl)-benzenesulphonamide was obtained as a white solid.

MS: (M+H)=611, (M−H)=609

$R_f$: 0.36 [methylene chloride/methanol/ammonia (90:10:1)]

g) Synthesis of (R)—N-(5-{2-[1,1-dimethyl-3-(4-phenylimidazol-1-yl)-propylamino]-1-hydroxyethyl}-2-hydroxy-phenyl)-benzenesulphonamide 0.10 g palladium (5% on activated charcoal) were added to. a solution of 0.30 g (0.41 mmol) (R)—N-(2-benzyloxy-5-{2-[1,1-dimethyl-3-(4-phenylimidazol-1-yl)-propylamino]-1-hydroxyethyl)phenyl)-benzenesulphonamide in 15 mL ethanol. The reaction mixture was shaken in an autoclave under a hydrogen pressure of 20 psi at ambient temperature for 3 h. The hydrogen pressure was released, the palladium was filtered off and the filtrate was freed from solvent using the rotary evaporator. The residue was purified by flash column chromatography [methylene chloride/methanol/ammonia (90:10:1)]. 0.20 g (0.31 mmol, 75%) (R)—N-(5-{2-[1,1-dimethyl-3-(4-phenylimidazol-1-yl)-propylamino]-1-hydroxyethyl}-2-hydroxy-phenyl)-benzenesulphonamide was obtained as a colourless solid.

MS: (M+H)=521, (M−H)=519

$R_f$: 0.33 [methylene chloride/methanol/ammonia (90:10:1)

EXAMPLE 5 a) Enantiomerically pure synthesis of (R)-1-(4-benzyloxy-3-nitrophenyl)-2-[1,1-dimethyl-3-(4-phenylimidazol-1-yl)-propylamino]-ethanol 0.90 g (3.1 mmol) of 3-chloro-1,1-dimethylpropylamine-hydrochloride were added to 10 mL sodium hydroxide solution (1 M) at 0° C. with vigorous stirring. The reaction mixture was stirred for 30 min at 0° C. and then combined with 20 mL methylene chloride. The phases were separated and the aqueous phase was extracted twice with 20 mL methylene chloride. The combined organic phases were dried over magnesium sulphate and the solvent was eliminated. The residue was dissolved in 5.0 mL methylene chloride and at ambient temperature combined with 0.70 g (2.6 mmol) (R)-2-(4-benzyloxy-3-nitrophenyl)-oxirane and 0.20 g (0.26 mmol) ytterbium (III) trifluoromethanesulphonate with stirring. The reaction mixture was stirred for 3 d at ambient temperature and then combined with 30 mL water/methylene chloride (1:1). The phases were separated and the aqueous phase was extracted twice with 20 mL methylene chloride. The combined organic phases were dried over magnesium sulphate and the-solvent was removed using the rotary evaporator. The residue was purified by flash column chromatography [methylene chloride/methanol/ammonia (90:10:1)]. 0.40 g (0.86 mmol, 33%) (R)-1-(4-benzyloxy-3-nitrophenyl)-2-[1,1-dimethyl-3-(4-phenylimidazol-1-yl)-propylamino]-ethanol was obtained as a yellowish solid.

MS: (M+H)=501, (M−H)=499

$R_f$: 0.27 [methylene chloride/methanol/ammonia (90:10:1)]

b) Enantiomerically pure synthesis of (R)-1-(3-amino-4-benzyloxyphenyl)-2-[1,1-dimethyl-3-(4-phenylimidazol-1-yl)-propylamino]-ethanol 0.025 g (0.11 mmol) platinum(IV)oxide were added to a solution of 0.15 g (0.28 mmol) (R)-1-(4-benzyloxy-3-nitrophenyl)-2-[1,1-dimethyl-3-(4-phenylimidazol-1-yl)-propylamino]-ethanol in 10 mL tetrahydrofuran/toluene (1:1). The reaction mixture was shaken in an autoclave under a hydrogen pressure of 10 psi at ambient temperature for 16 h. The hydrogen pressure was released, the platinum(IV)oxide was filtered off and the filtrate was freed from solvent using the rotary evaporator. 0.14 g (0.28 mmol, 99%) (R)-1-(3-amino-4-benzyloxyphenyl)-2-[1,1-dimethyl-3-(4-phenylimidazol-1-yl)-propylamino]-ethanol was obtained as a brown oil.

MS: (M+H)=471, (M−H)=469

$R_f$: 0.26 [ethyl acetate/methanol I ammonia (90:10:1)]

c) (R)—N-(2-benzyloxy-5-{2-[1,1-dimethyl-3-(4-phenylimidazol-1-yl)-propylamino]-1-hydroxyethyl}-phenyl)-benzenesulphonamide 0.10 mL (41 mmol) benzenesulphonic acid chloride were slowly added to a solution of 0.20 g (41 mmol) (R)-1-(3-amino-4-benzyloxyphenyl)-2-[1,1-dimethyl-3-(4-phenylimidazol-1-yl)-propylamino]-ethanol in 5 mL pyridine at 0° C. with vigorous stirring. After the addition was complete the reaction mixture was stirred for 4 h at 0° C. and then poured into 40 mL ice water/ethyl acetate (1:1). The phases were separated and the aqueous phase was extracted three times with 20 mL ethyl acetate. The combined organic phases were dried over magnesium sulphate and the solvent was removed using the rotary evaporator. 0.14 g (0.28 mmol, 99%) (R)—N-(2-benzyloxy-5-{2-[1,1-dimethyl-3-(4-phenylimidazol-1-yl)-propylamino]-1-hydroxyethyl}-phenyl)-benzenesulphonamide was obtained as a white solid.

MS: (M+H)=611, (M−H)=609

$R_f$: 0.36 [methylene chloride/methanol/ammonia (90:10:1)]

d) Enantiomerically pure synthesis of (R)—N-(5-{2-[1,1-dimethyl-3-(4-phenylimidazol-1-yl)-propylamino]-1-hydroxyethyl}-2-hydroxy-phenyl)-benzenesulphonamide 0.10 g palladium (5% on activated charcoal) were added to a solution of 0.30 g (0.41 mmol) (R)—N-(2-benzyloxy-5-{2-[1,1-dimethyl-3-(4-phenylimidazol-1-yl)-propylamino]-1-hydroxyethyl}-phenyl)-benzenesulphonamide in 15 mL ethanol. The reaction mixture was shaken in an autoclave under a hydrogen pressure of 20 psi at ambient temperature for 3 h. The hydrogen pressure was released, the palladium was filtered off and the filtrate was freed from solvent using the rotary evaporator. The residue was purified by flash column chromatography [methylene chloride/methanol/ammonia (90:10:1)]. 0.20 g (0.31 mmol, 75%) (R)-1-(4-benzyloxy-3-nitrophenyl)-2-[1,1-dimethyl-3-(4-phenylimidazol-1-yl)-propylamino]-ethanol was obtained as a colourless solid.

MS: (M+H)=521, (M–H)=519

R$_f$: 0.33 [methylene chloride/methanol/ammonia (90:10:1)]

e) Synthesis of (R)-1,2,3,4-tetrahydro-quinoline-8-sulphonic acid(5-{2-[1,1-dimethyl-3-(4-phenyl-imidazol-1-yl)-propylamino]-1-hydroxy-ethyl}-2-hydroxy-phenyl)-amide 0.10 g palladium (5% on activated charcoal) were added to a solution of 0.20 g (0.41 mmol) (R)-1,2,3,4-tetrahydro-quinoline-8-sulphonic acid (2-benzyloxy-5-{2-[1,1-dimethyl-3-(4-phenyl-imidazol-1-yl)-propylamino]-1-hydroxy-ethyl}-phenyl)-amide in 20 mL ethanol. The reaction mixture was shaken in an autoclave under a hydrogen pressure of 20 psi at ambient temperature for 6 h. The hydrogen pressure was released, the palladium filtered off and the filtrate was freed from solvent using the rotary evaporator. The residue was purified by flash column chromatography [methylene chloride/methanol/ammonia (90:10:1)]. 0.20 g (0.31 mmol, 75%) (R)-1,2,3,4-tetrahydro-quinoline-8-sulphonic acid(5-{2-[1,1-dimethyl-3-(4-phenyl-imidazol-1-yl)-propylamino]-1-hydroxy-ethyl}-2-hydroxy-phenyl)-amide were obtained as a colourless solid.

MS: (M+H)=576, (M–H)=574

R$_f$: 0.32 [methylene chloride/methanol/ammonia (90:10:1)]

EXAMPLE 12 a) Racemic synthesis of N-(2-benzyloxy-5{-2-[1,1-dimethyl-3-(4-phenyl-imidazol-1-yl)-propylamino]-1-hydroxy-ethyl)phenyl)methanesulphonamide 21.1 g (33.0 mmol) of N-[2-benzyloxy-5-(2-ethoxy-2-hydroxy-acetyl)-phenyl]-methanesulphonamide and 7.00 g (30.0 mmol) of 1,1-dimethyl-3-(4-phenyl-imidazol-1-yl)-propylamine in 150 mL ethanol were refluxed for 18 h. The reaction mixture was cooled to 0° C. and then combined with 3 g (77.0 mmol) sodium borohydride. It was stirred for a further 3 h at ambient temperature and then combined with glacial acetic acid. The solvent was removed using the rotary evaporator and the residue was dissolved in 300 mL ethyl acetate/water (1:2). The aqueous phase was made alkaline with conc. ammonia and separated from the organic phase. The organic phase was washed twice with 200 mL water and once with 200 mL of saturated, aqueous sodium chloride solution, dried over sodium sulphate and freed from solvent using the rotary evaporator. The residue was dissolved in 70 ml warm ethanol, combined with 5.4 g of oxalic acid and the oxalate formed was recrystallised from ethanol. 16.0 g (22.0 mmol, 73%) N-(2-benzyloxy-5{-2-[1,1-dimethyl-3-(4-phenyl-imidazol-1-yl)-propylamino]-1-hydroxy-ethyl)phenyl)methanesulphonamide were obtained as the oxalate.

Melting point: 183–184° C.

b) Racemic synthesis of N-(5-{2-[1,1-dimethyl-3-(4-phenyl-imidazol-1-yl)-propylamino]-1-hydroxy-ethyl}-2-hydroxy-phenyl)methanesulphonamide The base was liberated from 16.0 g of oxalate of N-(2-benzyloxy-5-{2-[1,1-dimethyl-3-(4-phenyl-imidazol-1-yl)-propylamino]-1-hydroxy-ethyl}-phenyl)methanesulphonamide by known methods.

1.5 g palladium (5% on activated charcoal) were added to a solution of the free base in 150 mL methanol. The reaction mixture was shaken in an autoclave under a hydrogen pressure of 20 psi at ambient temperature for 6 h. The hydrogen pressure was released, the palladium filtered off and the filtrate was freed from solvent using the rotary evaporator. The residue was recrystallised from acetonitrile. 3.9 g (93%) of N-(5-{2-[1,1-dimethyl-3-(4-phenyl-imidazol-1-yl)-propylamino]-1-hydroxy-ethyl}-2-hydroxy-phenyl)methanesulphonamide were obtained as a colourless solid.

Melting point: 133–136° C.

EXAMPLE 27 a) Racemic synthesis of N-(2-benzyloxy-5-1-hydroxy-2-[3-(4-iodimidazol-1-yl)-1,1-dimethyl-propylamino]-ethyl}-phenyl)-phenylsulphonamide 2.1 g (7.7 mmol) of 3-(4-iodimidazol-1-yl)-1,1-dimethyl-propylamine and 3.4 g (7.7 mmol) of N-[2-benzyloxy-5-(2-ethoxy-1,2-dihydroxy-ethyl)-phenyl]-phenylsulphonamide in 25 mL ethanol were refluxed for 18 h. The reaction mixture was cooled to 0° C. and then combined with 0.3 g (7.7 mmol) sodium borohydride. The mixture was stirred for a further 3 h at ambient temperature and then combined with glacial acetic acid. The solvent was removed using the rotary evaporator and the residue was dissolved in 300 mL ethyl acetate/water (1:2). The aqueous phase was made alkaline with conc. ammonia and separated from the organic phase. The organic phase was washed twice with 100 mL water and once with 100 mL of saturated aqueous sodium chloride solution, dried over sodium sulphate and freed from solvent using the rotary evaporator. The residue was purified by flash column chromatography [methylene chloride/methanol/ammonia (90:10:1)]. 3.5 g (5.0 mmol, 69%) N-(2-benzyloxy-5-{1-hydroxy-2-[3-(4-iodo-imidazol-1-yl)-1,1-dimethyl-propylamino]-ethyl}-phenyl)-phenylsulphonamide were obtained as a yellowish solid.

MS: (M+H)=661, (M–H)=659

R$_f$: 0.51 [methylene chloride/methanol/ammonia (90:10:1)]

b) Racemic synthesis of N-(2-benzyloxy-5-{2-[1,1-dimethyl-3-(4-phenyl-imidazol-1-yl)-propylamino]-1-hydroxy-ethyl)-phenyl)-phenylsulphonamide 0.500 g (0.757 mmol) of N-(2-benzyloxy-5q1-hydroxy-2-[3-(4-iodo-imidazol-1-yl)-1,1-dimethyl-propylamino]-ethyl}-phenyl)-phenylsulphonamide, 0.211 g (1.51 mmol) of 4-fluoro-phenylboric acid, 0.012 g (0.010 mmol) of tetrakis(triphenylphosphino)palladium and 0.010 g (0.010 mmol) of tetrabutylammonium bromide in 20 mL saturated, aqueous sodium hydrogen carbonate solution I toluene (1:1) were refluxed for 3 d. The reaction-mixture was combined with 100 mL toluene water (1:1) at ambient temperature, the phases were separated and the organic phase was washed three times with 50 mL water. The organic phase was dried over sodium sulphate and freed from solvent using the rotary evaporator. The residue was purified by flash column chromatography [methylene chloride/methanol (90:10)]. 0.420 g (0.668 mmol, 88%) N-(2-benzyloxy-5-{2-[1,1-dimethyl-3-(4-phenyl-imidazol-1-yl)-propylamino]-1-hydroxyethyl}-phenyl)-phenylsulphonamide were obtained as a colourless oil.

MS: (M+H)=629, (M–H)=627

R$_f$: 0.36 [methylene chloride/methanol (90:10)]

EXAMPLE 25 a) Racemic synthesis of 1-(4-benzyloxy-2-fluoro-phenyl)-2-[3-(4,5-diphenyl-imidazol-1-yl)-1,1-dimethyl-propylamino]-ethanol 12.2 g (40.0 mmol) of 1-(4-benzyloxy-2-fluoro-phenyl)-2-ethoxy-2-hydroxy-ethanone and 9.2 9 (30.0 mmol) 3-(4,5-diphenyl-imidazol-1-yl)-1,1-dimethyl-propylamine in 200 mL ethanol were refluxed for 18 h. The reaction mixture was cooled to 0° C. and then combined with 3 g (77.0 mmol) of sodium borohydride. The mixture was stirred for a further 3 h at ambient temperature and then combined with glacial acetic acid. The solvent was removed using the rotary evaporator and the residue was dissolved in 300 mL ethyl acetate/water (1:2). The aqueous phase was made alkaline with conc. ammonia and separated from the organic phase. The organic phase was washed twice with 200 mL water and once with 200 mL saturated, aqueous sodium chloride solution, dried over sodium sulphate and freed from solvent using the rotary evaporator. The residue was dissolved in 70 ml warm ethanol, combined with 3.5 g of fumaric acid and the fumarate obtained was recrystallised from ethanol. 11.0 g (20.0 mmol, 50%) 1-(4-benzyloxy-2-fluoro-phenyl)2-[3-(4,5-diphenyl-imidazol-1-yl)-1,1-dimethyl-propylamino]-ethanol were obtained as the fumarate.

Melting point: 182–183° C.

b) Racemic synthesis of 4-{2-[3-(4,5-diphenyl-imidazol-1-yl)-1,1-dimethyl-propylamino]-1-hydroxy-ethyl)-3-fluoro-phenol The base was liberated from 7.0 g of fumarate of 1-(4-benzyloxy-2-fluoro-phenyl)-2-[3-(4,5-diphenyl-imidazol-1-yl)-1,1-dimethyl-propylamino]-ethanol by known methods. 1.0 g palladium (5% on activated charcoal) were added to a solution of the free base in 100 mL methanol. The reaction mixture was shaken in an autoclave under a hydrogen pressure of 20 psi at ambient temperature for 6 h. The hydrogen pressure was released, the palladium was filtered off and the filtrate was freed from solvent using the rotary evaporator. The residue was recrystallised from acetonitrile. 3.9 g (93%) 4-2-[3-(4,5-diphenyl-imidazol-1-yl)-1,1-dimethyl-propylamino]-1-hydroxy-ethyl}-3-fluoro-phenol were obtained as a colourless solid.

Melting point: 163–165° C.

The compounds of formulae (IA), (IB) and (IC) listed in Tables 1, 2 and 3 are obtained, inter alia, analogously to the procedure described hereinbefore. The abbreviations $X_1$, $X_2$, $X_4$, $X_5$, $X_6$, $X_8$ and $X_{12}$ used in the Tables in each case denote a link to a position in the general formula shown under Table 1 instead of the corresponding groups $R^1$, $R^2$, $R^4$, $R^5$, $R^6$, $R^8$ and $R^{12}$.

TABLE 1-continued (IA)

| Ex. | R1 | R2 | R4 | R5 | R6 | R8 | R12 | stereo-chemistry* |
|---|---|---|---|---|---|---|---|---|
| 5 | X₁-NH-SO₂-(1,2,3,4-tetrahydroquinolin-8-yl) | H | X₄ CH₃ | X₅ H₃C | X₆-(1H-imidazol-1-yl), 4-phenyl | H | H | R |
| 6 | HN(X₁)-SO₂-(naphthalen-1-yl) | H | X₄ CH₃ | X₅ H₃C | X₆-(1H-imidazol-1-yl), 4-phenyl | H | H | R |
| 7 | X₁-NH-SO₂-(naphthalen-2-yl) | H | X₄ CH₃ | X₅ H₃C | X₆-(1H-imidazol-1-yl), 4-phenyl | H | H | R |
| 8 | CH₃-SO₂-NH-X₁ | H | H | H | X₆-(1H-imidazol-1-yl), 4-phenyl | CH₃-SO₂-X₆ | H | R |
| 9 | phenyl-SO₂-NH-X₁ | H | H | H | X₆-(1H-imidazol-1-yl), 4-phenyl | H | H | R |
| 10 | CH₃-SO₂-NH-X₁ | H | H | H | X₆-(1H-imidazol-1-yl), 4-phenyl | H | H | R |
| 11 | X₁-NH-SO₂-CH₃ | H | H | X₅ CH₃ | X₆-(1H-imidazol-1-yl), 4-phenyl | H | H | R |

TABLE 1-continued (IA)

| Ex. | R1 | R2 | R4 | R5 | R6 | R8 | R12 | stereo-chemistry* |
|-----|----|----|----|----|----|----|-----|-------------------|
| 12 | X₁-NH-SO₂-CH₃ | H | CH₃ (X₄) | H₃C-X₅ | X₆-N-imidazole-phenyl | H | H | rac |
| 13 | H₃C-C(O)-NH-X₁ | H | X₄-CH₃ | H₃C-X₅ | X₆-N-triazole-C₆H₄-OCH₃ | H | H | R |
| 14 | X₁-NH-SO₂-CH₃ | H | X₄-CH₃ | H₃C-X₅ | X₆-N-imidazole-phenyl | H | X₁₂-CH₂-phenyl | R |
| 15 | X₁-NH-SO₂-CH₃ | H | X₄-CH₃ | H₃C-X₅ | X₆-N-imidazole-phenyl | H | H | R |
| 16 | X₁-NO₂ | H | X₄-CH₃ | H₃C-X₅ | X₆-N-imidazole-C₆H₄-OCH₃ | H | X₁₂-CH₂-phenyl | R |
| 17 | X₁-NH₂ | H | X₄-CH₃ | H₃C-X₅ | X₆-N-imidazole-C₆H₄-OCH₃ | H | X₁₂-CH₂-phenyl | R |
| 18 | X₁-NH-SO₂-CH₃ | H | X₄-CH₃ | H₃C-X₅ | X₆-N-imidazole-C₆H₄-OCH₃ | H | X₁₂-CH₂-phenyl | R |
| 19 | X₁-NH-SO₂-CH₃ | H | X₄-CH₃ | H₃C-X₅ | X₆-N-imidazole-C₆H₄-OCH₃ | H | H | R |

TABLE 1-continued (IA)

| Ex. | R1 | R2 | R4 | R5 | R6 | R8 | R12 | stereo-chemistry* |
|---|---|---|---|---|---|---|---|---|
| 20 | X1-HN-S(=O)2-CH(CH3)CH3 (isopropylsulfonamide) | H | X4-CH3 | X5-CH3 | imidazole-phenyl-OCH3 | H | X12-CH2-phenyl (benzyl) | S |
| 21 | X1-HN-S(=O)2-CH(CH3)CH3 | H | X4-CH3 | X5-CH3 | imidazole-phenyl-OCH3 | H | H | S |
| 22 | X1-NH-S(=O)2-CH3 | H | X4-CH3 | CH3, X5-CH3 | imidazole-phenyl-OCH3 | H | H | S |
| 23 | X1-NH-S(=O)2-CH3 | H | X4-CH3 | X5-CH3 | imidazole-phenyl | H | H | S |
| 24 | X1-NH-S(=O)2-CH3 | H | X4-CH3 | H3C-X5 | 4,5-diphenylimidazole (X5 on N) | H | H | rac |
| 25 | H | F | X4-CH3, H3C | H3C-X5 | 4,5-diphenyl-imidazoline | H | H | rac |
| 26 | H | F | X4-CH3, H3C | H3C-X5 | imidazole-phenyl | H | H | rac |
| 27 | phenyl-S(=O)2-NH-X1 (benzenesulfonamide) | H | H3C-X5 | H3C-X5 | imidazole-phenyl-F | H | X12-CH2-phenyl (benzyl) | rac |

TABLE 1-continued (IA)

| Ex. | R1 | R2 | R4 | R5 | R6 | R8 | R12 | stereo-chemi-stry* |
|---|---|---|---|---|---|---|---|---|
| 28 | phenyl-SO$_2$-NH-X$_1$ | H | H$_3$C-X$_5$ | H$_3$C-X$_5$ | X$_6$-imidazolyl-(4-fluorophenyl) | | H | H | rac |

TABLE 2

(IB)

| Example | R1 | molecular weight determined by mass spectrometry |
|---|---|---|
| 29 | 2-(trifluoromethyl)phenylsulfonyl-X$_1$ | 589 |
| 30 | 3-chlorophenylsulfonyl-X$_1$ | 555 |
| 31 | 5-(pyridin-2-yl)thiophen-2-ylsulfonyl-X$_1$ | 604 |
| 32 | 2,6-dichlorophenylsulfonyl-X$_1$ | 589 |

TABLE 2-continued
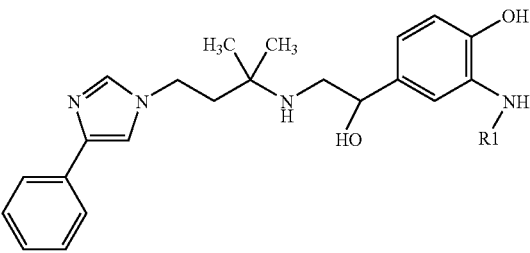
(IB)
| Example | R1 | molecular weight determined by mass spectrometry |
|---|---|---|
| 33 | 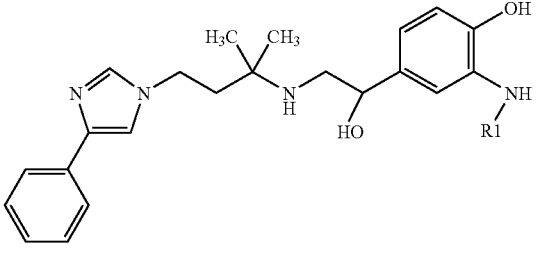 | 605 |
| 34 | 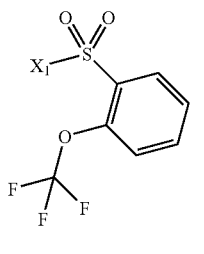 | 573 |
| 35 | 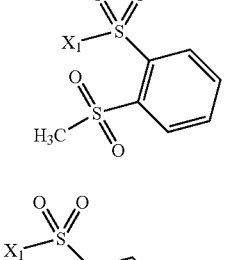 | 597 |
| 36 | 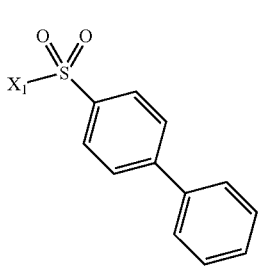 | 625 |
| 37 | 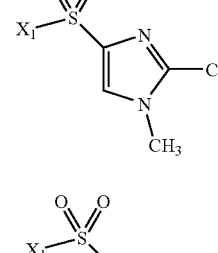 | 599 |
| 38 | 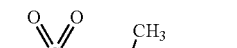 | 599 |
| 39 | 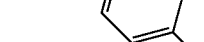 | 563 |
| 40 | 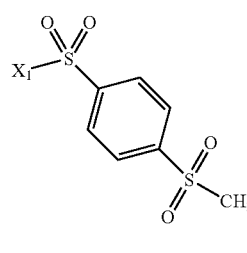 | 539 |
| 41 |  | 535 |
| 42 | 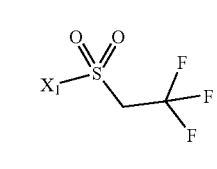 | 547 |
| 43 | | 525 |

TABLE 2-continued
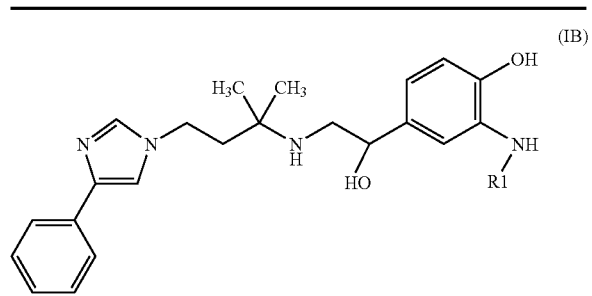
(IB)
| Example | R1 | molecular weight determined by mass spectrometry |
|---|---|---|
| 44 | 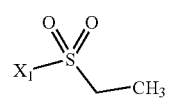 | 473 |
| 45 | 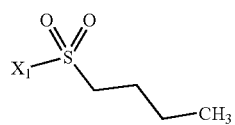 | 501 |
| 46 | 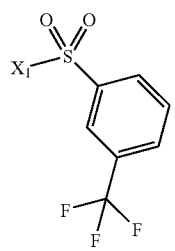 | 589 |
| 47 | 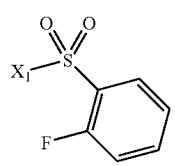 | 539 |
| 48 | 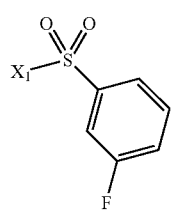 | 539 |
| 49 | 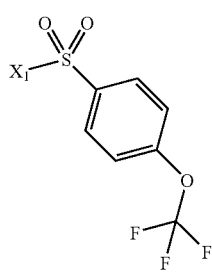 | 605 |
TABLE 2-continued
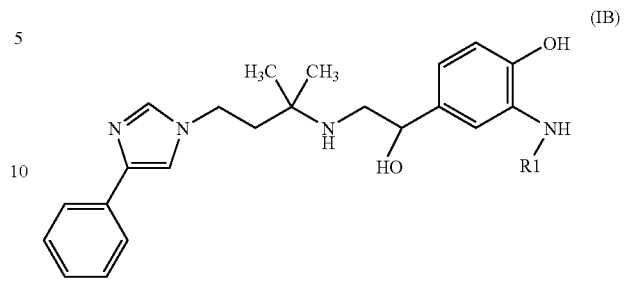
(IB)
| Example | R1 | molecular weight determined by mass spectrometry |
|---|---|---|
| 50 | 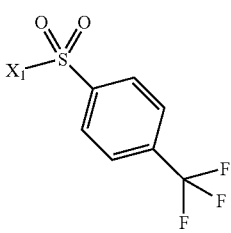 | 589 |
| 51 | 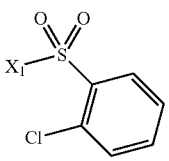 | 555 |
| 52 |  | 614 |
| 53 | 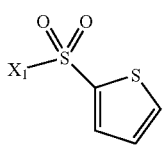 | 527 |
| 54 | 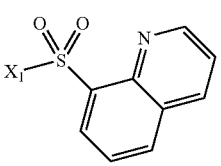 | 662 |
| 55 | 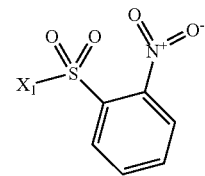 | 566 |

TABLE 2-continued
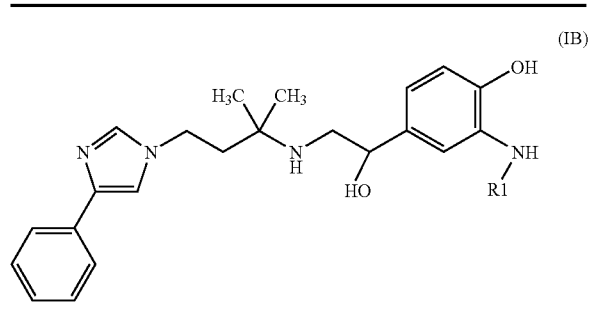
(IB)
| Example | R1 | molecular weight determined by mass spectrometry |
|---|---|---|
| 56 | 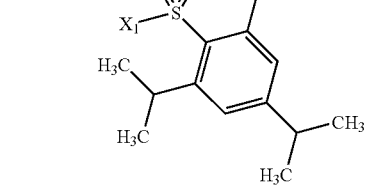 | 647 |
| 57 | 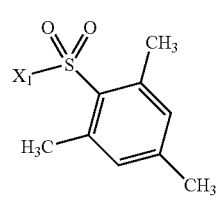 | 563 |
| 58 | 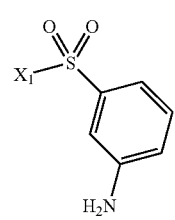 | 536 |
| 59 | 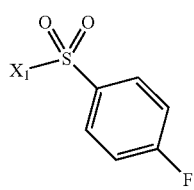 | 539 |
| 60 | 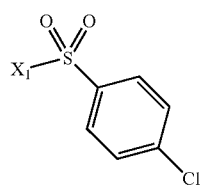 | 555 |
TABLE 2-continued
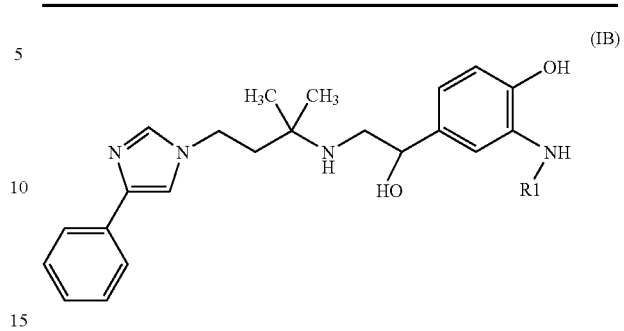
(IB)
| Example | R1 | molecular weight determined by mass spectrometry |
|---|---|---|
| 61 | 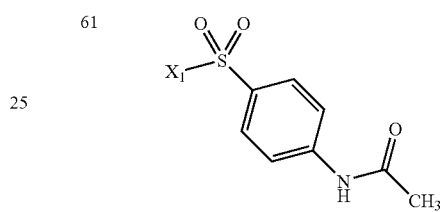 | 578 |
| 62 | 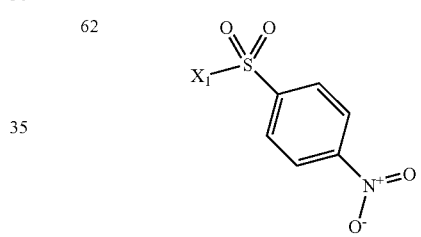 | 566 |
| 63 | 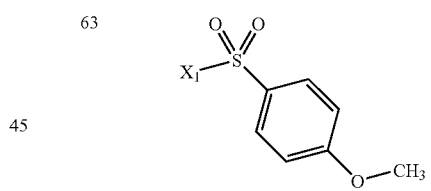 | 551 |
| 64 | 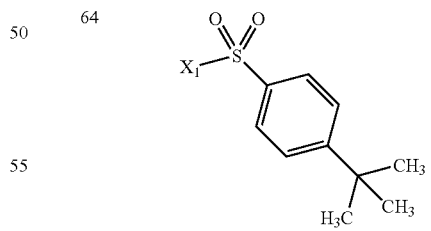 | 577 |
| 65 | 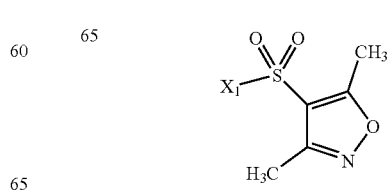 | 539 |

TABLE 2-continued (IB)

[Structure: imidazole-phenyl with H3C, CH3, NH, HO, OH, NHR1 substituents]

| Example | R1 | molecular weight determined by mass spectrometry |
|---|---|---|
| 66 | X1-SO2-(3-methylphenyl) | 535 |
| 67 | X1-SO2-cyclopropyl | 485 |
| 68 | X1-SO2-(furan-2-yl) | 601 |
| 69 | X1-SO2-(thiophen-3-yl) | 527 |
| 70 | X1-SO2-N(2-methylpyrrolidinyl) | 528 |
| 71 | X1-SO2-N(pyrrolidinyl) | 514 |
| 72 | X1-SO2-N(CH2CH3)2 | 516 |
| 73 | X1-SO2-N(morpholinyl) | 528 |
| 74 | X1-SO2-(4-aminophenyl) | 536 |
| 75 | X1-SO2-(2-aminophenyl) | 534 |

TABLE 3

(IC)

[Structure: imidazole-phenyl with H3C, CH3, NH, HO, OH, NHSO2-phenyl substituents, R1 on imidazole]

| Example | R1 | molecular weight determined by mass spectrometry |
|---|---|---|
| 76 | X1-(3-nitrophenyl) | 566 |

TABLE 3-continued (IC)

| Example | R1 | molecular weight determined by mass spectrometry |
|---|---|---|
| 77 | 1-naphthyl | 571 |
| 78 | 4-chlorophenyl | 555 |
| 79 | 4-methylphenyl | 535 |
| 80 | 3-methylphenyl | 535 |
| 81 | 3,5-bis(trifluoromethyl)phenyl | 657 |
| 82 | 3,5-dichlorophenyl | 589 |
| 83 | 4-biphenyl | 597 |
| 84 | 4-phenoxyphenyl | 613 |

TABLE 3-continued (IC)

| Example | R1 | molecular weight determined by mass spectrometry |
|---|---|---|
| 85 | 4-(methylthio)phenyl | 567 |
| 86 | 2-methylphenyl | 535 |
| 87 | 4-carboxyphenyl | 565 |
| 88 | 2-thienyl | 527 |
| 89 | 3-thienyl | 527 |
| 90 | 3-chlorophenyl | 555 |
| 91 | 3,5-dimethylphenyl | 549 |
| 92 | 2-benzofuranyl | 561 |
| 93 | 3-fluorophenyl | 539 |
| 94 | 2-naphthyl | 571 |

TABLE 3-continued (IC) structure: imidazole-CH2-C(CH3)2-NH-CH(OH)-phenyl(OH)-NH-SO2-phenyl, with R1 on imidazole

| Example | R1 | molecular weight determined by mass spectrometry |
|---|---|---|
| 95 | 2-(trifluoromethyl)phenyl | 589 |
| 96 | 2-fluorophenyl | 539 |
| 97 | 2-furyl | 511 |
| 98 | 3,4-difluorophenyl | 557 |
| 99 | 2,6-dimethylphenyl | 549 |
| 100 | 1,3-benzodioxol-5-yl | 565 |
| 101 | 4-(trifluoromethoxy)phenyl | 605 |
| 102 | benzothiophen-2-yl | 577 |
| 103 | benzothiophen-3-yl | 577 |
| 104 | 3,5-difluorophenyl | 557 |
| 105 | 3-cyanophenyl | 546 |
| 106 | 2,4-difluorophenyl | 557 |
| 107 | 3-(trifluoromethoxy)phenyl | 605 |
| 108 | 4-acetamidophenyl | 578 |
| 109 | 4-aminophenyl | 536 |

As has been found, the compounds of general formula (I) are characterised by their great versatility in the therapeutic field. Particular mention should be made of those applications in which the effects of beta-3-agonists, particularly selective beta-3-agonists play a part.

Such diseases include for example:

atherosclerosis, cholangitis, gall bladder disease, chronic cystitis, chronic bladder inflammation; chronic prostatitis, cystospaz, depression, duodenal ulcer, duodenitis, dysmenorrhoea; increased intraocular pressure and glaucoma, enteritis, oesophagitis, gastric ulcer, gastritis, gastrointestinal disorders caused by contraction(s) of the smooth muscle, gastrointestinal disorders incl. gastric ulcer; gastrointestinal ulceration, gastrointestinal ulcers, glaucoma, glucosuria, hyperanakinesia, hypercholesterolaemia, hyperglycaemia, hyperlipaemia, arterial hypertension, hypertriglyceridaemia, insulin resistance, intestinal ulceration or small bowel ulcers (incl. inflammatory bowel diseases, ulcerative colitis, Crohn's disease and proctitis=inflammation of the rectum), irritable colon and other diseases with decreased intestinal motility, depression, melancholy, pollacisuria, frequent urinary urgency, nervous neurogenic inflammation, neurogenic bladder dysfunction, neurogenic inflammation of the respiratory tract, neuropathic bladder dysfunction, nycturia, non-specific diarrhoea, dumping syndrome, obesity, fatness, pancreatitis, inflammation of the pancreas, stomach ulcers, prostate diseases such as benign prostatic hyperplasia, enlarged prostate, spasm, cramp, type 2 diabetes mellitus, irritable bladder or concrement of the lower urinary tract.

The beta-3 agonists according to the invention are particularly suitable for the treatment of obesity, insulin resistance; type 2 diabetes mellitus; urinary incontinence; irritable colon and other diseases with decreased intestinal motility or depression, particularly for the treatment of diabetes and obesity. The activity of the beta-3 agonists can be determined for example in a lipolysis test. The test procedure may be carried out as follows:

Adipocytes were isolated from fatty tissue ex vivo by modifying a method according to Rodbell (Rodbell, M. Metabolism of isolated fat cells. I. Effects of hormones on glucose metabolism and lipolysis. *J Biol Chem* 239: 375–380. 1964). The excised fatty tissue was cut into small pieces and mixed with 1 mg/ml collagenase in Krebs Ringer Buffer (KRB) containing 6 mM glucose and 2% albumin by gently shaking for 30–40 min at 37° C. The cells were filtered through a gauze, washed twice with KRB and in each case 50–150 g were centrifuged for 5 min. 10 µl of the centrifuged adipocytes were incubated with 90 µl of a compound according to the invention (agonist) at concentrations of between $10^{-15}$ to $10^{-4}$ M. The agonists were incubated over 40 min at 37° C. A varying release of glycerol in the medium indicated that the fat cell lipolysis had altered as a result of the addition of the agonist. Released glycerol was detected enzymatically with a Sigma kit (triglyceride (GPO Trinder) Reagent A; Cat. #337–40A), as described below.

Glycerol is phosphorylated by ATP via glycerol kinase. The resulting glycerol-1-phosphate is oxidised by glycerol-phosphate oxidase to form dihydroxyacetone phosphate and hydrogen peroxide. Then a quinonimine dye is produced by the peroxidase-catalysed coupling of sodium-N-ethyl-N-(3-sulphopropyl)m-ansidine and 4-aminoantipyrine. The dye has an absorption peak at 540 nm. The absorption is directly proportional to the glycerol concentration in the samples.

The new compounds may be used for the prevention or short-term or long-term treatment of the above-mentioned diseases, and may also be used in conjunction with other active substances used for the same indications. These include, for example, antidiabetics, such as metformin, sulphonylureas (e.g. glibenclamid, tolbutamide, glimepiride), nateglinide, repaglinide, thiazolidine-dione (e.g. rosiglitazone, pioglitazone), PPAR-gamma agonists (e.g. GI 262570), alpha-glucosidase inhibitors (e.g. acarbose, voglibose), alpha2 antagonists, insulin and insulin analogues, GLP-1 and GLP-1 analogues (e.g. exendin-4) or amylin. Also, inhibitors of protein tyrosine phosphatase 1, substances which influence deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents, such as HMG-CoA-reductase inhibitors (e.g. simvastatin, atorvastatin), fibrates (e.g. bezafibrate, fenofibrate), nicotinic acid and its derivatives, cholesterol absorption inhibitors such as for example ezetimibe, bile acid-binding substances such as for example cholestyramine, HDL-raising compounds such as for example inhibitors of CETP or regulators of ABC1 or active substances for the treatment of obesity, such as e.g. sibutramine or tetrahydrolipostatin.

In particular, they may also be combined with drugs for treating high blood pressure such as e.g. All antagonists or ACE inhibitors, diuretics, β-blockers, and other modulators of the adrenergic system or combinations thereof. In addition, combinations with stimulators of the adrenergic system via alpha 1 and alpha 2 and also beta 1, beta 2 and beta 3 receptors are particularly suitable.

The compounds of general formula (I) may be used on their own or in conjunction with other active substances according to the invention, optionally also in conjunction with other pharmacologically active substances. Suitable preparations include for example tablets, capsules, suppositories, solutions,—particularly solutions for injection (s.c., i.v., i.m.) and infusion—elixirs, emulsions or dispersible powders. The content of the pharmaceutically active compound(s) should be in the range from 0.1 to 90 wt. %, preferably 0.5 to 50 wt. % of the composition as a whole, i.e. in amounts which are sufficient to achieve the dosage range specified below. The specified doses may be taken several times a day, if necessary.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, optionally organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, preferably oral. For oral administration the tablets may, of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1–1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation Examples which follow illustrate the present invention without restricting its scope:

EXAMPLES OF PHARMACEUTICAL FORMULATIONS

| A) Tablets | per tablet |
|---|---|
| active substance | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A method for treating a disease or condition selected from the group consisting of obesity, insulin resistance; type 2 diabetes mellitus; urinary incontinence and irritable colon, said method comprising administering to a host in need of such treatment a therapeutically effective amount of f a compound of formula I

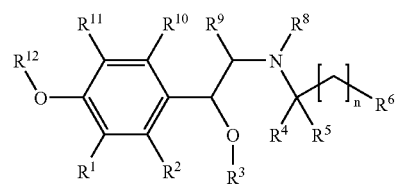

wherein
$R^1$, $R^2$, $R^{10}$, $R^{11}$ independently of one another denote a group selected from among hydrogen, halogen, CN, $NO_2$, and $-NHCXNH_2$ or a group selected from among optionally substituted $-COR^7$, $-COOR^7$, $-CONR^7R^{13}$, $-OR^{14}$, $NR^{13}R^{15}$, $C_1-C_{10}$-alkyl, $C_3-C_8$-cycloalkyl, $-NR^{16}CX-R^{17}$, $-NR^{18}CX-OR^{19}$, $-NR^{20}SO_mR^{21}$, $-SO_pNR^{22}R^{23}$ and $-SO_qR^{24}$
m, p, q denotes 0, 1 or 2
n denotes 0, 1, 2 or 3
$R^3$ denotes hydrogen or a group selected from among optionally substituted $C_1-C_{10}$-alkyl, $C_6-C_{10}$-aryl, heterocyclyl and $C_3-C_8$-cycloalkyl, $-CX-C_1-C_{10}$-alkyl and $-CX-C_6-C_{14}$-aryl, $R^4$, $R^5$ independently of one another denote hydrogen, halogen or optionally substituted $C_1$–$C_{10}$-alkyl, or $R^4$ and $R^5$ together denote a $C_3$–$C_8$-alkyl bridge, $R^6$ denotes a group of formula

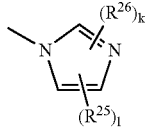

l,k independently of one another denote 1,2 or 3, $R^{25}$, $R^{26}$ independently of one another denote a group selected from among hydrogen, OH, halogen, CN and $NO_2$, or a group selected from among optionally substituted $C_1$–$C_{10}$-alkyl, $C_6$–$C_{18}$-aryl, heteroaryl, heterocyclyl, —CX—$R^{17}$, —$OR^{14}$, $NR^{13}R^{15}$, $C_3$–$C_8$-cycloalkyl —$NR^{20}SO_mR^{21}$, —$SO_pNR^{22}R^{23}$, —$SO_qR^{24}$, —$NR^{18}CX$—$R^{19}$ and —$NR^{18}CXOR^{17}$, while $R^{25}$ and $R^{26}$ cannot simultaneously denote hydrogen, $R^8$ denotes hydrogen or a group selected from among optionally substituted $C_1$–$C_{10}$-alkyl, $C_6$–$C_{18}$-aryl, —$SO_q$—$C_1$–$C_{10}$-alkyl, —$SO_q$—$C_6$–$C_{14}$-aryl, —CX—$C_1$–$C_{10}$-alkyl, —CX—$C_6$–$C_{14}$-aryl, $C_6$–$C_{10}$-aryl, heterocyclyl and $C_3$–$C_8$-cycloalkyl $R^9$ denotes hydrogen or a group selected from among optionally substituted $C_1$–$C_{10}$-alkyl, $C_6$–$C_{14}$-aryl, heteroaryl, $C_3$–$C_8$-cycloalkyl and heterocycloalkyl, $R^{12}$ denotes hydrogen or a group selected from among optionally substituted benzyl, $C_1$–$C_{12}$-alkyl and $C_6$–$C_{14}$-aryl, $R^7$, $R^{13}$, $R^{15}$, $R^{16}$, $R^{18}$, $R^{20}$ $R^{22}$, $R^{23}$ independently of one another denote hydrogen, or a group selected from among optionally substituted $C_1$–$C_{10}$-alkyl, $C_6$–$C_{14}$-aryl, heterocyclyl and $C_3$–$C_8$-cycloalkyl $R^{14}$, $R^{19}$, $R^{29}$ independently of one another denote hydrogen or a group selected from among optionally substituted $C_1$–$C_{10}$-alkyl, $C_6$–$C_{14}$-aryl, $C_3$–$C_8$-cycloalkyl, heteroaryl, heterocyclyl, —$CXNR_{13}R_{15}$ and —$CXR_7$ $R^{17}$ denotes a group selected from among $C_1$–$C_{10}$-alkyl, $C_6$–$C_{14}$-aryl, heterocyclyl, heteroaryl and $C_3$–$C_8$-cycloalkyl $R^{21}$, $R^{24}$ independently denote hydrogen or OH, or a group selected from among optionally substituted $N(C_1$–$C_{10}$-alkyl$)_2$, $N(C_3$–$C_8$-cycloalkyl), $C_1$–$C_{10}$-alkyl, $C_6$–$C_{14}$-aryl, heterocyclyl, heteroaryl and $C_3$–$C_8$-cycloalkyl and X denotes O, S or $NR^{29}$, or a pharmaceutically acceptable salt thereof.

2. The method according to claim 1, wherein:

$R^{10}$, $R^{11}$ independently of one another denote hydrogen or halogen, m, p, q independently of one another denote 0, 1 or 2 n denotes 0, 1, 2 or 3

$R^3$ denotes hydrogen or $C_1$–$C_5$-alkyl $R^4$, $R^5$ independently of one another denote hydrogen or $C_1$–$C_5$-alkyl, $R^8$ denotes a group selected from among hydrogen, $C_1$–$C_5$-alkyl, —$SO_q$—$C_1$–$C_5$-alkyl, —$SO_q$—$C_6$–$C_{14}$-aryl, phenyl and $C_3$–$C_6$-cycloalkyl $R^9$ denotes hydrogen or $C_1$–$C_{10}$-alkyl $R^{12}$ denotes hydrogen or benzyl $R^{13}$, $R^{15}$, $R^{16}$, $R^{18}$ independently of one another denote a group selected from among hydrogen, $C_1$–$C_5$-alkyl, $C_3$–$C_6$-cycloalkyl and phenyl $R^{14}$, $R^{19}$ independently of one another denote hydrogen or $C_1$–$C_5$-alkyl, and $R^{17}$ denotes optionally substituted $C_1$–$C_5$-alkyl or $C_6$–$C_{10}$-aryl.

3. The method according to claim 1, wherein $R^{10}$ $R^{11}$ denote hydrogen m, p, q denote 0, 1 or 2 n denotes 0, 1, 2 or 3

$R^3$ denotes hydrogen $R^4$, $R^5$ independently of one another denote hydrogen or methyl, $R^8$ denotes hydrogen, —$SO_q$—$C_6$–$C_{14}$-aryl or —$SO_2$—$C_1$–$C_5$-alkyl $R^9$ denotes hydrogen $R^{12}$ denotes hydrogen or benzyl, $R^{13}$, $R^{15}$, $R^{16}$, $R^{18}$ independently of one another denote a group selected from among hydrogen, $C_1$–$C_{15}$-alkyl and phenyl, $R^{14}$, $R^{19}$ independently of one another denote hydrogen or $C_1$–$C_5$-alkyl, and $R^{17}$ denotes $C_1$–$C_5$-alkyl or $C_6$–$C_{14}$-aryl.

4. The method according to claim 1, wherein $R^1$ denotes a group selected from among hydrogen, $NO_2$, $NH_2$, —NHCX—$R^{17}$ and —$NHSO_2R^{21}$ $R^2$ denotes hydrogen or halogen n denotes 2, $R^3$ denotes hydrogen $R^4$, $R^5$ denote hydrogen or methyl $R^6$ denotes a group of formula

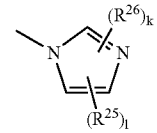

l,k denote 1

$R^{26}$ denotes hydrogen, $R^8$ denotes hydrogen or —$SO_2CH_3$, $R^9$ denotes hydrogen, $R^{10}$, $R^{11}$ denote hydrogen, and $R^{12}$ denotes hydrogen or benzyl.

5. The method according to claim 4, wherein $R^6$ denotes an optionally substituted group of the formula (j)

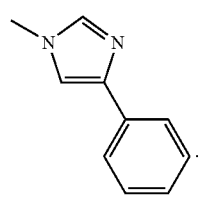

6. The method according to claim 1, 2, 3, 4 or 5 wherein the condition to be treated is selected from the group consisting of obesity, insulin resistance and type 2 diabetes mellitus.

* * * * *